United States Patent [19]

Danchin et al.

[11] Patent Number: 5,183,745
[45] Date of Patent: Feb. 2, 1993

[54] ADENYL CYCLASE DERIVATIVES AND THEIR BIOLOGICAL USES

[75] Inventors: Antoine Danchin; Philippe Glaser, both of Paris; Evelyne Krin, Colombes; Octavien Barzu, Massy; Daniel Ladant, Cachan; Agnés Ullmann, Paris, all of France

[73] Assignee: Institut Pasteur, Paris, France

[21] Appl. No.: 426,541

[22] Filed: Oct. 25, 1989

[30] Foreign Application Priority Data

Oct. 25, 1988 [FR] France ................................ 88 13951

[51] Int. Cl.⁵ .......................... C12P 21/06; C12N 9/88; C12N 15/00; C07H 15/12
[52] U.S. Cl. .................................... 435/69.1; 435/232; 435/172.1; 435/172.3; 935/10; 935/14; 536/23.2
[58] Field of Search ................... 435/232, 172.1, 172.2, 435/3, 69.1; 424/94.5; 935/14, 10; 536/27

[56] References Cited

FOREIGN PATENT DOCUMENTS 0235474  9/1987  European Pat. Off. .
0275689  7/1988  European Pat. Off. .

OTHER PUBLICATIONS

Holland, et al., "Isolation and Characterization of a Small Catalytic Domain . . . " *Journ. Bio. Chem.* 263 (29):14661–68.
Ladant, Daniel, "Interaction of Bondetella Pertussis Adenylate Cyclase with Calmodulin" *J. Biol. Chem.* 263 (6): 2612–2618.
Glaser et al., "The Calmodulin-Sensitive Adenylate Cyclase of Bordetella Pertussis: . . . " *Mol. Microb.* 1988 2 (1): 19–30.
Burnette et al., Pertusis Toxin S1 Mutant with Reduced Enzyme Activity and a Conserved Protective Epitope, Science, 242:72–74 (1988).
Ladant et al., Bordetella Pertussis Adenylate Cyclase, J. Biol. Chem., 261 (34):16264–16269 (1986).
Tippetts et al., Molecular Cloning and Expression of the Bacillus Anthracis Edema Factor Toxin Gene: A Calmodulin-Dependent Adenylate Cyclase, J. Bacteriol., 170(5):2263–2266 (1988).
Weiss et al., Tn5-Induced Mutations Affecting Virulence Factors of Bordetella Pertussis, Infection and Immunity, 42:33–41 (1983).
Glaser et al., Indentification of Residues Essential for Catalysis and Binding of Calmodulin in Bordetella Pertussis Adenylate Cyclase by Site-Directed Mutagenesis, EMBO J. 8(3):967–972 (1989).
Au et al., Site-Directed Mutagenesis of Lysine 58 in a Putative ATP-Binding Domain of the Calmodulin-Sensitive Adenylate Cyclase from Bordetella Pertussis Abolishes Catalytic Activity, Biochemistry, 28:2772–2776 (1989).

*Primary Examiner*—Robert A. Wax
*Assistant Examiner*—Keith D. Hendricks
*Attorney, Agent, or Firm*—Finnegan, Henderson, Farabow et al.

[57] ABSTRACT

The adenyl cyclase derivatives are atoxic derivatives in which one or several amino acids are different from those present in the toxic protein, the antibodies formed against these derivatives recognize, however, the toxic protein. These derivatives can be used as vaccines.

18 Claims, 18. Drawing Sheets

Fig. 1a

```
BamHI
GGATCCAAATTTTCCGGATTGGTGGGAATTTGTGCATTTTCACTGCGAATGTTGGAATAA
     .         .         .         .         .         .

TTTCGCCCATCGTCATACGACATGCTGGATGTTTGGTTCTTGCAGAAGGATGAGGTTCTG
     .         .         .        100         .         .

AGCGCTACACACCGGTTGCGTCGGTGCGAATCCGTTCAATCGACTACTTATCGACAGATC

HisMetGlnGlnSerHisGlnAlaGlyTyrAlaAsnAlaAlaAspArgGluSerGlyIle
CACATGCAGCAATCGCATCAGGCTGGTTACGCAAACGCCGCCGACCGGGAGTCTGGCATC
     .        200         .         .         .         .
ProAlaAlaValLeuAspGlyIleLysAlaValAlaLysGluLysAsnAlaThrLeuMet
CCCGCAGCCGTACTCGATGGCATCAAGGCCGTGGCGAAGGAAAAAAACGCCACATTGATG
     .         .         .         .         .        300
PheArgLeuValAsnProHisSerThrSerLeuIleAlaGluGlyValAlaThrLysGly
TTCCGCCTGGTCAACCCCCATTCCACCAGCCTGATTGCCGAAGGGGTGGCCACCAAAGGA
     .         .         .         .         .         .
LeuGlyValHisAlaLysSerSerAspTrpGlyLeuGlnAlaGlyTyrIleProValAsn
TTGGGCGTGCACGCCAAGTCGTCCGATTGGGGGTTGCAGGCGGGCTACATTCCCGTCAAC
     .         .         .        400         .         .
ProAsnLeuSerLysLeuPheGlyArgAlaProGluValIleAlaArgAlaAspAsnAsp
CCGAATCTTTCCAAACTGTTCGGCCGTGCGCCCGAGGTGATCGCGCGGGCCGACAACGAC
     .         .         .         .         .         .
ValAsnSerSerLeuAlaHisGlyHisThrAlaValAspLeuThrLeuSerLysGluArg
GTCAACAGCAGCCTGGCGCATGGCCATACCGCGGTCGACCTGACGCTGTCGAAAGAGCGG
     .        500         .         .         .         .
LeuAspTyrLeuArgGlnAlaGlyLeuValThrGlyMetAlaAspGlyValValAlaSer
CTTGACTATCTGCGGCAAGCGGGCCTGGTCACCGGCATGGCCGATGGCGTGGTCGCGAGC
     .         .         .         .         .        600
AsnHisAlaGlyTyrGluGlnPheGluPheArgValLysGluThrSerAspGlyArgTyr
AACCACGCAGGCTACGAGCAGTTCGAGTTTCGCGTGAAGGAAACCTCGGACGGGCGCTAT
     .         .         .         .         .         .
AlaValGlnTyrArgArgLysGlyGlyAspAspPheGluAlaValLysValIleGlyAsn
GCCGTGCAGTATCGCCGCAAGGGCGGCGACGATTTCGAGGCGGTCAAGGTGATCGGCAAT
     .         .         .        700         .         .
AlaAlaGlyIleProLeuThrAlaAspIleAspMetPheAlaIleMetProHisLeuSer
GCCGCCGGTATTCCACTGACGGCGGATATCGACATGTTCGCCATTATGCCGCATCTGTCC
                                 EcoRV
     .         .         .         .         .         .
AsnPheArgAspSerAlaArgSerSerValThrSerGlyAspSerValThrAspTyrLeu
AACTTCCGCGACTCGGCGCGCAGTTCGGTGACCAGCGGCGATTCGGTGACCGATTACCTG
     .        800         .         .         .         .
AlaArgThrArgArgAlaAlaSerGluAlaThrGlyGlyLeuAspArgGluArgIleAsp
GCGCGCACGCGGCGGGCCGCCAGCGAGGCCACGGGCGGCCTGGATCGCGAACGCATCGAC
     .         .         .         .         .        900
```

Fig. 1b

```
LeuLeuTrpLysIleAlaArgAlaGlyAlaArgSerAlaValGlyThrGluAlaArgArg
TTGTTGTGGAAAATCGCTCGCGCCGGCGCCCGTTCCGCAGTGGGCACCGAGGCGCGTCGC

GlnPheArgTyrAspGlyAspMetAsnIleGlyValIleThrAspPheGluLeuGluVal
CAGTTCCGCTACGACGGCGACATGAATATCGGCGTGATCACCGATTTCGAGCTGGAAGTG
                                  .       1000
ArgAsnAlaLeuAsnArgArgAlaHisAlaValGlyAlaGlnAspValValGlnHisGly
CGCAATGCGCTGAACAGGCGGGCGCACGCCGTCGGCGCGCAGGACGTGGTCCAGCATGGC

ThrGluGlnAsnAsnProPheProGluAlaAspGluLysIlePheValValSerAlaThr
ACTGAGCAGAACAATCCTTTCCCGGAGGCAGATGAGAAGATTTTCGTCGTATCGGCCACC
             .      1100       .       .       .       .
GlyGluSerGlnMetLeuThrArgGlyGlnLeuLysGluTyrIleGlyGlnGlnArgGly
GGTGAAAGCCAGATGCTCACGCGCGGGCAACTGAAGGAATACATTGGCCAGCAGCGCGGC
                                  .       .       1200
GluGlyTyrValPheTyrGluAsnArgAlaTyrGlyValAlaGlyLysSerLeuPheAsp
GAGGGCTATGTCTTCTACGAGAACCGTGCATACGGCGTGGCGGGGAAAAGCCTGTTCGAC

AspGlyLeuGlyAlaAlaProGlyValProSerGlyArgSerLysPheSerProAspVal
GATGGGCTGGGAGCCGCGCCCGGCGTGCCGAGCGGACGTTCGAAGTTCTCGCCGGATGTA
     .       .       .       1300      .       .       .
LeuGluThrValProAlaSerProGlyLeuArgArgProSerLeuGlyAlaValGluArg
CTGGAAACGGTGCCGGCGTCACCCGGATTGCGGCGGCCGTCGCTGGGCGCAGTGGAACGC

GlnAspSerGlyTyrAspSerLeuAspGlyValGlySerArgSerPheSerLeuGlyGlu
CAGGATTCCGGCTATGACAGCCTTGATGGGGTGGGATCGCGATCGTTCTCGTTGGGCGAG
         .       1400      .       .       .       .       .
ValSerAspMetAlaAlaValGluAlaAlaGluLeuGluMetThrArgGlnValLeuHis
GTGTCCGACATGGCCGCCGTGGAAGCGGCGGAACTGGAAATGACCCGGCAAGTCTTGCAC
                                          .       .       1500
AlaGlyAlaArgGlnAspAspAlaGluProGlyValSerGlyAlaSerAlaHisTrpGly
GCCGGGGCGCGGCAGGACGATGCCGAGCCGGGCGTGAGCGGTGCGTCGGCGCACTGGGGG

GlnArgAlaLeuGlnGlyAlaGlnAlaValAlaAlaAlaGlnArgLeuValHisAlaIle
CAGCGGGCGCTGCAGGGCGCCCAGGCGGTGGCGGCGGCGCAGCGGCTGGTTCATGCCATT
                         .       1600      .       .       .
AlaLeuMetThrGlnPheGlyArgAlaGlySerThrAsnThrProGlnGluAlaAlaSer
GCCCTGATGACGCAATTCGGCCGGGCCGGTTCCACCAACACGCCGCAGGAAGCGGCCTCG

LeuSerAlaAlaValPheGlyLeuGlyGluAlaSerSerAlaValAlaGluThrValSer
TTGTCGGCGGCCGTGTTCGGCTTGGGCGAGGCCAGCAGCGCCGTGGCCGAAACCGTGAGC
         .       1700      .       .       .       .       .
GlyPhePheArgGlySerSerArgTrpAlaGlyGlyPheGlyValAlaGlyGlyAlaMet
GGTTTTTTCCGCGGGTCTTCGCGCTGGGCCGGCGGTTTCGGCGTGGCTGGCGGCGCGATG
                                      .       .       1800
```

Fig. 1c

```
AlaLeuGlyGlyGlyIleAlaAlaAlaValGlyAlaGlyMetSerLeuThrAspAspAla
GCGCTGGGAGGCGGCATCGCCGCGGCCGTTGGCGCCGGGATGTCGTTGACCGATGACGCG

ProAlaGlyGlnLysAlaAlaAlaGlyAlaGluIleAlaLeuGlnLeuThrGlyGlyThr
CCGGCCGGACAGAAGGCCGCCGCCGGCGCCGAGATCGCGCTGCAGTTGACAGGTGGAACG
                                 1900
ValGluLeuAlaSerSerIleAlaLeuAlaLeuAlaAlaAlaArgGlyValThrSerGly
GTCGAGCTGGCTTCTTCCATCGCGTTGGCGCTGGCCGCGGCGCGCGGCGTGACCAGCGGC

LeuGlnValAlaGlyAlaSerAlaGlyAlaAlaAlaGlyAlaLeuAlaAlaAlaLeuSer
TTGCAGGTGGCCGGGGCGTCGGCCGGGGCGGCTGCCGGCGCATTGGCCGCGGCGCTCAGT
           2000
ProMetGluIleTyrGlyLeuValGlnGlnSerHisTyrAlaAspGlnLeuAspLysLeu
CCCATGGAGATCTACGGCCTGGTGCAGCAATCGCACTATGCGGATCAGCTGGACAAGCTG
                                                       2100
AlaGlnGluSerSerAlaTyrGlyTyrGluGlyAspAlaLeuLeuAlaGlnLeuTyrArg
GCGCAGGAATCGAGCGCATACGGTTACGAGGGCGACGCCTTGCTGGCCCAGCTGTATCGC

AspLysThrAlaAlaGluGlyAlaValAlaGlyValSerAlaValLeuSerThrValGly
GACAAGACGGCCGCCGAGGGCGCCGTCGCCGGCGTCTCCGCCGTCCTGAGCACGGTGGGG
                               2200
AlaAlaValSerIleAlaAlaAlaAlaSerValValGlyAlaProValAlaValValThr
GCGGCGGTGTCGATCGCCGCGGCGGCCAGCGTGGTAGGGGCCCCGGTGGCGGTGGTCACT

SerLeuLeuThrGlyAlaLeuAsnGlyIleLeuArgGlyValGlnGlnProIleIleGlu
TCCTTGCTGACCGGGGCTCTCAACGGCATCCTGCGCGGCGTGCAGCAGCCCATCATCGAA
           2300
LysLeuAlaAsnAspTyrAlaArgLysIleAspGluLeuGlyGlyProGlnAlaTyrPhe
AAGCTGGCCAACGATTACGCTCGCAAGATCGACGAGCTGGGCGGGCCGCAAGCGTACTTC
                                                       2400
GluLysAsnLeuGlnAlaArgHisGluGlnLeuAlaAsnSerAspGlyLeuArgLysMet
GAGAAAAACCTGCAGGCGCGTCACGAACAACTGGCCAATTCGGACGGCCTACGGAAAATG

LeuAlaAspLeuGlnAlaGlyTrpAsnAlaSerSerValIleGlyValGlnThrThrGlu
CTGGCCGACCTGCAGGCCGGTTGGAACGCCAGCAGCGTGATCGGGGTGCAGACGACAGAG
                                     2500
IleSerLysSerAlaLeuGluLeuAlaAlaIleThrGlyAsnAlaAspAsnLeuLysSer
ATCTCCAAGTCGGCGCTCGAACTGGCCGCCATTACCGGCAACGCGGACAACCTGAAATCC

ValAspValPheValAspArgPheValGlnGlyGluArgValAlaGlyGlnProValVal
GTCGACGTGTTCGTGGACCGCTTCGTCCAGGGCGAGCGGGTGGCCGGCCAGCCGGTGGTC
                        2600
LeuAspValAlaAlaGlyGlyIleAspIleAlaSerArgLysGlyGluArgProAlaLeu
CTCGACGTCGCCGCCGGCGGCATCGATATCGCCAGCCGCAAGGGCGAGCGGCCGGCGCTG
                               EcoRV
                                                       2700
```

Fig. 1d

```
ThrPheIleThrProLeuAlaAlaProGlyGluGluGlnArgArgArgThrLysThrGly
ACGTTCATCACGCCGCTGGCCGCGCCAGGAGAAGAGCAGCGCCGGCGCACGAAAACGGGC

LysSerGluPheThrThrPheValGluIleValGlyLysGlnAspArgTrpArgIleArg
AAGAGCGAATTCACCACATTCGTCGAGATCGTGGGCAAGCAGGACCGCTGGCGCATCCGG
      EcoRI
                             2800
AspGlyAlaAlaAspThrThrIleAspLeuAlaLysValValSerGlnLeuValAspAla
GACGGCGCGGCCGACACCACCATCGATCTGGCCAAGGTGGTGTCGCAACTGGTCGACGCC

AsnGlyValLeuLysHisSerIleLysLeuAspValIleGlyGlyAspGlyAspAspVal
AATGGCGTGCTCAAGCACAGCATCAAACTGGATGTGATCGGCGGAGATGGCGATGACGTC
             2900
ValLeuAlaAsnAlaSerArgIleHisTyrAspGlyGlyAlaGlyThrAsnThrValSer
GTGCTTGCCAATGCTTCGCGCATCCATTATGACGGCGGCGCGGGCACCAACACGGTCAGC
                                                  3000
TyrAlaAlaLeuGlyArgGlnAspSerIleThrValSerAlaAspGlyGluArgPheAsn
TATGCCGCCCTGGGTCGACAGGATTCCATTACCGTGTCCGCCGACGGGGAACGTTTCAAC

ValArgLysGlnLeuAsnAsnAlaAsnValTyrArgGluGlyValAlaThrGlnThrThr
GTGCGCAAGCAGTTGAACAACGCCAACGTGTATCGCGAAGGCGTGGCTACCCAGACAACC
                         3100
AlaTyrGlyLysArgThrGluAsnValGlnTyrArgHisValGluLeuAlaArgValGly
GCCTACGGCAAGCGCACGGAGAATGTCCAATACCGCCATGTCGAGCTGGCCCGTGTCGGG

GlnValValGluValAspThrLeuGluHisValGlnHisIleIleGlyGlyAlaGlyAsn
CAAGTGGTGGAGGTCGACACGCTCGAGCATGTGCAGCACATCATCGGCGGGGCCGGCAAC
        3200
AspSerIleThrGlyAsnAlaHisAspAsnPheLeuAlaGlyGlySerGlyAspAspArg
GATTCGATCACCGGCAATGCGCACGACAACTTCCTAGCCGGCGGGTCGGGCGACGACAGG
                                            3300
LeuAspGlyGlyAlaGlyAsnAspThrLeuValGlyGlyGluGlyGlnAsnThrValIle
CTGGATGGCGGCGCCGGCAACGACACCCTGGTTGGCGGCGAGGGCCAAAACACGGTCATC

GlyGlyAlaGlyAspAspValPheLeuGlnAspLeuGlyValTrpSerAsnGlnLeuAsp
GGCGGCGCCGGCGACGACGTATTCCTGCAGGACCTGGGGGTATGGAGCAACCAGCTCGAT
                         3400
GlyGlyAlaGlyValAspThrValLysTyrAsnValHisGlnProSerGluGluArgLeu
GGCGGCGCGGGCGTCGATACCGTGAAGTACAACGTGCACCAGCCTTCCGAGGAGCGCCTC

GluArgMetGlyAspThrGlyIleHisAlaAspLeuGlnLysGlyThrValGluLysTrp
GAACGCATGGGCGACACGGGCATCCATGCCGATCTTCAAAAGGGCACGGTCGAGAAGTGG
            3500
ProAlaLeuAsnLeuPheSerValAspHisValLysAsnIleGluAsnLeuHisGlySer
CCGGCCCTGAACCTGTTCAGCGTCGACCATGTCAAGAATATCGAGAATCTGCACGGCTCC
                                            3600
```

Fig. 1e

```
ArgLeuAsnAspArgIleAlaGlyAspAspGlnAspAsnGluLeuTrpGlyHisAspGly
CGCCTAAACGACCGCATCGCCGGCGACGACCAGGACAACGAGCTCTGGGGCCACGATGGC
                                           SacI

AsnAspThrIleArgGlyArgGlyGlyAspAspIleLeuArgGlyGlyLeuGlyLeuAsp
AACGACACGATACGCGGCCGGGGCGGCGACGACATCCTGCGCGGCGGCCTGGGCCTGGAC
                                    3700
ThrLeuTyrGlyGluAspGlyAsnAspIlePheLeuGlnAspAspGluThrValSerAsp
ACGCTGTATGGCGAGGACGGCAACGACATCTTCCTGCAGGACGACGAGACCGTCAGCGAT

AspIleAspGlyGlyAlaGlyLeuAspThrValAspTyrSerAlaMetIleHisProGly
GACATCGACGGCGGCGCGGGGCTGGACACCGTCGACTACTCCGCCATGATCCATCCAGGC
                     3800
ArgIleValAlaProHisGluTyrGlyPheGlyIleGluAlaAspLeuSerArgGluTrp
AGGATCGTTGCGCCGCATGAATACGGCTTCGGGATCGAGGCGGACCTGTCCAGGGAATGG
                                                        3900
ValArgLysAlaSerAlaLeuGlyValAspTyrTyrAspAsnValArgAsnValGluAsn
GTGCGCAAGGCGTCCGCGCTGGGCGTGGACTATTACGATAATGTCCGCAATGTCGAAAAC

ValIleGlyThrSerMetLysAspValLeuIleGlyAspAlaGlnAlaAsnThrLeuMet
GTCATCGGTACGAGCATGAAGGATGTGCTCATCGGCGACGCGCAAGCCAATACCCTGATG
                                    4000
GlyGlnGlyGlyAspAspThrValArgGlyGlyAspGlyAspAspLeuLeuPheGlyGly
GGCCAGGGCGGCGACGATACCGTGCGCGGCGGCGACGGCGATGATCTGCTGTTCGGCGGC

AspGlyAsnAspMetLeuTyrGlyAspAlaGlyAsnAspThrLeuTyrGlyGlyLeuGly
GACGGCAACGACATGCTGTATGGCGACGCCGGCAACGACACCCTCTACGGGGGGCTGGGC
          4100
AspAspThrLeuGluGlyGlyAlaGlyAsnAspTrpPheGlyGlnThrGlnAlaArgGlu
GACGATACCCTTGAAGGCGGCGCGGGCAACGATTGGTTCGGCCAGACGCAGGCGCGCGAG
                                                   4200
HisAspValLeuArgGlyGlyAspGlyValAspThrValAspTyrSerGlnThrGlyAla
CATGACGTGCTGCGCGGCGGAGATGGGGTGGATACCGTCGATTACAGCCAGACCGGCGCG

HisAlaGlyIleAlaAlaGlyArgIleGlyLeuGlyIleLeuAlaAspLeuGlyAlaGly
CATGCCGGCATTGCCGCGGGTCGCATCGGGCTGGGCATCCTGGCTGACCTGGGCGCCGGC
                                    4300
ArgValAspLysLeuGlyGluAlaGlySerSerAlaTyrAspThrValSerGlyIleGlu
CGCGTCGACAAGCTGGGCGAGGCCGGCAGCAGCGCCTACGATACGGTTTCCGGTATCGAG

AsnValValGlyThrGluLeuAlaAspArgIleArgAlaMetArgArgProThrCysCys
AACGTGGTGGGCACGGAACTGGCCGACCGCATCCGGGCGATGCGCAGGCCAACGTGCTGC
          4400
AlaAlaArgValAlaProThrCysLeuArgAlaAlaArgAlaThrMetCysCysTrpAla
GCGGCGCGGGTGGCGCCGACGTGCTTGCGGGCGGCGAGGGCGACGATGTGCTGCTGGGCG
                                                   4500
```

Fig. 1f

```
AlaThrAlaThrThrSerCysArgAlaThrProAspAlaIleAlaCysThrAlaLysPro
GCGACGGCGACGACCAGCTGTCGGGCGACGCCGGACGCGATCGCTTGTACGGCGAAGCCG

ValThrThrGlySerSerArgMetProProMetProAlaAsnLeuLeuAspGlyGlyAsp
GTGACGACTGGTTCTTCCAGGATGCCGCCAATGCCGGCGAATCTGCTCGACGGCGGCGAC
                                  4600
GlyArgAspThrValAspGlnArgPro
GGCCGCGATACCGTGGATCAGCGCCCGGG
                         SmaI
```

Fig. 2

```
              10         20         30         40         50
     MTRNKFIPNKFSIISFSVLLFAISSSQAIEVNAMNEHYTESDIKRNHKTEKNKTEKEKFK 70         80         90        100        110
     DSINNLVKTEFTNETLDKIQQTQDLLKKIPKDVLEIYSELGGEIYFTDIDLVEHKELQDL 130        140        150        160        170
     SEEEKNSMNSRGEKVPFASRFVFEKKRETPKLIINIKDYAINSEQSKEVYYEIGKGISLD 190        200        210        220        230
     IISKDKSLDPEFLNLIKSLSDDSDSSDLLFSQKFKEKLELNNKSIDINFIKENLTEFQHA 250        260        270        280        290
     FSLAFSYYFAPDHRTVLELYAPDMFEYMNKLEKGGFEKISESLKKEGVEKDRIDVLKGEK
                                                    +    +    ++
                                                    MQQSHQAGYANA
                                                              10

310        320        330        340        350
     ALKASGLVPEHADAFKKIARELNTYILFRPVNKLATNLIKSGVATKGLNVHGKSSDWGPV
     * + **+ +    *+ * +*+* *+ ++** **  +* **  ******* **+**** *
     ADRESGIPAAVLDGIKAVAKEKNATLMFRLVNPHSTSLIAEGVATKGLGVHAKSSDWGLQ
           20         30         40         50         60         70

370        380        390        400        410
     AGYIPFDQDLSKKHGQQLAVEKGNLENKKSITEHEGEIGKIPLKLDHLRIEELKENGIIL
     ***** + +***  *       * ++  *   * *  + + * * + *++ *++ *++
     AGYIPVNPNLSKLFGRAPEVIARADNDVNSSLAH-GHTA-VDLTLSKERLDYLRQAGLVT
           80         90        100        110        120

430        440        450       460        470
     KGKKEIDNGKKYYLLESNNQVYEFRISDENNE---VQYKTKEGKITVLGEKFNWRNIEVM
      *  +   +      *    +****+ + +    ***+  *    *+ *    * +
     -GMADGVVASNHAGYEQ----FEFRVKETSDGRYAVQYRRKG------GDDF-----EAV
                140        150        160                170

480        490        500        510        520
     AKNVEGVLKPLTADYDLFALAPSLTEIKKQIPQKEWD-------KVVNTPNSLEKQKGV-
        ++     ***** *+++* * *++ +                   + *   *+
     KVIGNAAGIPLTADIDMFAIMPHLSNFRDSARSSVTSGDSVTDYLARTRRAASEATGGLD
          180        190        200        210        220        230

530        540        550        560        570
     ---TNLLIKY--GIE-RKPDSTKGTLSNWQKQM---LDRLNEAV-KYTGYTGGDVVNHGT
        +** *    * * *+    * + *          *+  *    +  + ++ ***+***
     RERIDLLWKIARGTEARRQFRYDGDM-NIGVITDFELEVRNALNRRAHAVGAQDVVQHGT
          240        250        260        270        280        290
```

Fig. 2 (cont.)

```
      580         590  α    600          610          620          630
     EQDNEEFPEKDNEIFIINPEGEF-ILTKNWEMTGRFIEKNITGKDYLYYFNRSYNKIAPG
     **+*    *** *+ **++ + ** +**+ ++   +* +  *  *++* +*+* +* *
     EQNNP-FPEADEKIFVVSATGESQMLTRG-QLKE-YIGQQR-GEGYVFYENRAY-GVA-G
           310         320         330        340         350

640         650         660          670         680  β    690
     NKAYIE---WTDP-ITKAKINTIPTSAEFIKNLSSIRRSSNVGVYK-DSGDKDEFAKKES
     *+  +    + * ++ ++    *  * +  +++**+* ++ + ***  *          *
     -KSLFDDGLGAAPGVPSGRSKFSPDVLETVPASPGLRRPSLGAVERQDSG-YDSLDGVGS
           360         370         380         390        400         410

700         710         720         730         740         750
     VKKIAGYLSDYYNSANHIFSQEKKRKISIFRGIQAYNEIENVLKSKQIAPEYKNYFQYLK
        *  +**         +         +    +  *  +*   +                +
     RSFSLGEVSDMAAVEAAELEMTRQVLHAGARQDDAEPGVSGASAHWGQRALQGAQAVAAA
           420         430         440         450         460         470

760         770         780         790
     ERITNQVQLLLTHQKSNIEFKLLYKQLNFTENETDNFEVFQKIIDEK
     +*+       +*    ++             +      +
     QRLVHAIALMTQFGRAGSTNTPQEAASLSAAVFGLGEASSAVAETVSGFFRGSSRWAGGF
           480         490         500         510         520         530
```

Fig. 3A

```
TGCGATCATTCGGCATGTACGGTCCAGCTGCCGCGAGCGGCCGCCGCGTCCAGCGCCCTCGGTACTCCTTGACGCGCCGGTGTCGCCGCCGAACGCGCAGCGAACGGCC
         10        20        30        40        50        60        70        80        90       100       110       120

CACGCTGTCGGGGTGTTCGGCCGCCAGCGCCCGGGCAGCGCCGACGATTGTCGTCGCCGAGAATGGCCGCATCCAGTCGATGATCCACAGTCGGTGCCGCAGTTCCAGGCATTCCCGCC
        130       140       150       160       170       180       190       200       210       220       230       240

CAGCGACGAGGGCCATGACGATAGGAGAGTTCGGTGTCGGCGTCCATTAGGGCCCAGCTGCAACCGGCACGTCATTGCATCGCAGCAGAATGTATTGGCCCAGTTGAATCGG
        250       260       270       280       290       300       310       320       330       340       350       360

CGGGAGCGCTGTTGCGTGCCGAGCAGATGACGGCCAGTCGCATGGAGCAATATTGCCCAGTGCCGCGAAGTCGTCGGTGGGATTGAGGAGGGAGG
        370       380       390       400       410       420       430       440       450       460       470       480

GCCCTTGGGCGGACGAAGCATGACATCGTGTCATGTGAGCGGGGCATATTCCGTCTGTTGGGTGCCGCATGGACAAGCGCCGGCATCATGGTTGCGCGGAATGGCTTTTCTTA
        490       500       510       520       530       540       550       560       570       580       590       600

CATGTTTCCAGGATATGTCCGTATTTCGGGCGATGCCTCCGGTCCGCGGCATGCCTCCGGTGCCGCCTGCTTTTGTGTCGAACATGTGCAATGTGTTGTCCGATCGCGTTGTCGCCGATCCGGTCGTTGGCCGTTGGCCGCTTGCTCTCGCCGCTTATTATCTCCC
        610       620       630       640       650       660       670       680       690       700       710       720

TTGAAGCCTTGTTCTCTTTTCATTAGAAAGAAATATGCGCTTTGTGTTTAGGATGATTTCCTGTCCGAGTAGGGTGGATCCAAATTTTCCGGATTGGTGGGAATTTGTGCATTTTCAC
        730       740       750       760       770       780       790       800       810       820       830       840
```

Fig. 3B

```
TGCGAATGTTGGAATAATTTCGCCCATCGTCATACGACACTGGATGTTGGTTCTTGCAGAAGGATGAGGTTCTGAGCGCTACACACCGGTTGCTCGTGCGAATCCGTCAATCGA
    850       860       870       880       890       900       910       920       930       940       950       960

M  Q  Q  S  H  Q  A  G  Y  A  N  A  A  D  R  E  S  G  I  P  A  A  V  L  D  G  I  K  A  V  A  K  E  K
CTACTTATCGACACAGATCCACATGCAGCAGCAATCGCATCAGGCTGGTTACGCAAACGCCGCCGACGGGAGTCTGGCATCCCCAGCCGTACTCGATGGCATCAAGGCCGTGGCGAAGGAAA
    970       980       990      1000      1010      1020      1030      1040      1050      1060      1070      1080

N  A  T  L  M  F  R  L  V  N  P  H  S  T  S  L  I  A  E  G  V  A  T  K  G  L  G  V  H  A  K  S  S  D  W  G  L  Q  A  G
AAAACGCCACATTGATGTTCCGCCTGGTCAACCCCCATTCCACCAGCTCACTGCCGAAGGGATTGCCACCAAGGGTGCCACCAAGACCCTGATCACACCAAGTCGTCGATTGGGGGTTGCAGGCGG
   1090      1100      1110      1120      1130      1140      1150      1160      1170      1180      1190      1200

Y  I  P  V  N  P  N  L  S  K  L  F  G  R  A  P  E  V  I  A  R  A  D  N  D  V  N  S  S  L  A  H  G  H  T  A  V  D  L  T
GCTACATTCCCGTCAACCCGAATCTTTCCAAACTGTTCGGCCGTGCGCCGAGGTGATCGCGCGAGGCGAGACAATGACGTCAACAGCAGCCTGGCGCATGCCGGCCATACCGCGGTCGACCTGA
   1210      1220      1230      1240      1250      1260      1270      1280      1290      1300      1310      1320

L  S  K  E  R  L  D  Y  L  R  Q  A  G  L  V  T  G  M  A  D  G  V  V  A  S  N  H  A  G  Y  E  Q  F  E  F  R  V  K  E  T
CGGTGTCGAAAGAGCGGCTTGACTATCTGCGCCAGGCCGGCCTTGTCACCGGGGCATGGCCGATGGCGTGGTCGCGAGCAACCACGCAGGCTACGAGCAGTTCGAGTTCCGCGTGAAGGAAA
   1330      1340      1350      1360      1370      1380      1390      1400      1410      1420      1430      1440

S  D  G  R  Y  A  V  Q  Y  R  R  K  G  G  D  D  F  E  A  V  K  V  I  G  N  A  A  G  I  P  L  T  A  D  I  D  M  F  A  I
CCTCGGACGGCCGCTATGCCGTGCAGTATCGCCGCAAGGGCGGCGACGATTTCGAGGCGGTCAAGGTGATCGGCAATGCCGCCGGTATTCCACTGACGGCGGATATCGACATGTTCGCCA
   1450      1460      1470      1480      1490      1500      1510      1520      1530      1540      1550      1560
```

Fig. 3C

```
M  P  H  L  S  N  F  R  D  S  A  R  S  S  V  T  S  G  D  S  V  T  D  Y  L  A  R  T  R  R  A  A  S  E  A  T  G  G  L  D
TTATGCCGATCTGTCCAACTTCCGCGACTCGGCGCGCAGTTCGGTGACCAGCGGGGATTCGGTGACCGATTACCTGGCGCGCACCCGCCGGGCGGCCAGCGAGGCCACGGGCCTGG
         1580      1590      1600      1610      1620      1630      1640      1650      1660      1670      1680

R  E  R  I  D  L  L  W  K  I  A  R  A  G  A  R  S  A  V  G  T  E  A  R  R  Q  F  R  Y  D  G  D  M  N  I  G  V  I  T  D
ATCGCGAACGGCATCGACTTGTTGTGGAAAATCGCTCGCGCGGGCGCCCGTTCCGCAGTGGGCACCGAGGCGCGTCGCCAGTTCCGCTACGACGGCGACATGAATATCGGCGTGATCACCG
         1700      1710      1720      1730      1740      1750      1760      1770      1780      1790      1800

F  E  L  E  V  R  N  A  L  N  R  R  A  H  A  V  G  A  Q  D  V  V  Q  H  G  T  E  Q  N  N  P  F  P  E  A  D  E  K  I  F
ATTTCGAGCTGGAAGTGCGCAATGCGCTGAACAGGCGGGCGCACGCCGTCGGCGCGCAGGACGTGGTCCAGCATGGCACTGAGCAGAACAATCCTTTCCCGGAGGCAGATGAGAAGATT
         1820      1830      1840      1850      1860      1870      1880      1890      1900      1910      1920

V  V  S  A  T  G  E  S  Q  M  L  T  R  G  Q  L  K  E  Y  I  G  Q  Q  R  G  E  G  Y  V  F  Y  E  N  R  A  Y  G  V  A  G
TCGTCGTATGCCACCGGTGAAAGCCAGATGCTCACCCGCGGCCAACTGAAGGAATACATTGGCCAGCAGCGCGGAGGCTATGTCTTCTACGAACGTGCATACGGGGTGGCCGG
         1940      1950      1960      1970      1980      1990      2000      2010      2020      2030      2040

K  S  L  F  D  D  G  L  G  A  A  P  G  V  P  S  G  R  S  K  F  S  P  D  V  L  E  T  V  P  A  S  P  G  L  R  R  P  S  L
GGAAAAGGCTGTTCGACGATGGGCTGGGAGCCGCCCCCGGCGTGCCCGAGCGGACGTTCTCCCCGGATGTACTGGAAACGGTGCCGGCGTCACCCGGATTGCGGCGGCCGTCGC
         2060      2070      2080      2090      2100      2110      2120      2130      2140      2150      2160
```

Fig. 3D

```
 G  A  V  E  R  Q  D  S  G  Y  D  S  L  D  G  V  G  S  R  S  F  S  L  G  E  V  S  D  M  A  A  V  E  A  A  E  L  E  M  T
TGGGCGCAGTGGAACGCCAGGATTCCGGCTATGACAGCCTTGATGGGTGGAGTCGCGATCGTTCTCGTTGGGCGAGGAGGTGTCCGACATGGCCGCCGTGGAAGCGGCGGAACTGGAAATGA
    2170      2180      2190      2200      2210      2220      2230      2240      2250      2260      2270      2280

R  Q  V  L  H  A  G  A  R  Q  D  D  A  E  P  G  V  S  G  A  S  A  H  W  G  Q  R  A  L  Q  G  A  Q  A  V  A  A  A  Q  R
CCCGGCAAGTCTTGCACGCCGGGGCGGCAGACGATGCCGAGCCGGGTGTCGGGCGCGTCGAGCGGCCACTGGGGCAGCGGCGCCCTGCAGGGCGCCCAGGCGGTGGCGGCGGCGCAGC
    2290      2300      2310      2320      2330      2340      2350      2360      2370      2380      2390      2400

L  V  H  A  I  A  L  M  T  Q  F  G  R  A  G  S  T  N  T  P  Q  E  A  A  S  L  S  A  A  V  F  G  L  G  E  A  S  S  A  V
GGCTGGTTCATGCCATTGCCCTGATGACGCAATTCGGCCGGGCCGGTTCCACCAACACGCCGCAGGAAGGCCTCGTTGTCGGCGGTCGTGTTCGGCGGTTGGGCGAGGCCAGCAGCGGCCG
    2410      2420      2430      2440      2450      2460      2470      2480      2490      2500      2510      2520

A  E  T  V  S  G  F  F  R  G  S  S  R  W  A  G  G  F  G  V  A  G  G  A  M  A  L  G  G  G  I  A  A  A  V  G  A  G  M  S
TGGCCGAAACCGTGAGCGGTTTTTTCCGCGGGTCTTCCGCCGTGGAGCGGCATCGCCGGCGTTGGCGCCGGGATGT
    2530      2540      2550      2560      2570      2580      2590      2600      2610      2620      2630      2640

L  T  D  D  A  P  A  G  Q  K  A  A  A  G  A  E  I  A  L  Q  L  T  G  G  T  V  E  L  A  S  S  I  A  L  A  L  A  A  A  R
CGTTGACCGATGACGCGCCGGCCGGACAGAAGGCCGCCGCCGGCGCCGAGATCGCGCTGCAGTTGACACAGGTGGAACGGTCGAGCTGGCTTCTTCCATCGCGTTGGCGCTGGCCGGCGC
    2650      2660      2670      2680      2690      2700      2710      2720      2730      2740      2750      2760
```

Fig. 3E

```
G  V  T  S  G  L  Q  V  A  G  A  S  A  G  A  A  A  G  A  L  A  A  A  L  S  P  M  E  I  Y  G  L  V  Q  Q  S  H  Y  A  D
GCGGGCGTGACCAGCGGCTTGCAGGTGGCCGGTGCCTCCGCGGGCGCTGCCGGCGGGGCGCTGGCCGCTGCAGTCCCATGGAGATCTACGGCCTGGTGCAGCAATCGCACTATGCGG
     2770      2780      2790      2800      2810      2820      2830      2840      2850      2860      2870      2880

Q  L  D  K  L  A  Q  E  S  S  A  Y  G  Y  E  G  D  A  L  L  A  Q  L  Y  R  D  K  T  A  A  E  G  A  V  A  G  V  S  A  V
ATCAGCTGGACAAGCTGGCGCAGGAATCGAGCGCATACGGTTACGAGGGCGACGCCTTGCTGGCCCAGCTGTATCGCGACAAGACCGCCGCCGAGGGCGCCGTCGCCGGTGTCTCCGCCG
     2890      2900      2910      2920      2930      2940      2950      2960      2970      2980      2990      3000

L  S  T  V  G  A  A  V  S  I  A  A  A  A  S  V  V  G  A  P  V  A  V  V  T  S  L  L  T  G  A  L  N  G  I  L  R  G  V  Q
TCCTGAGCACCGTGGGGGCGGCGGTGTCGATCGCCGCGGCGGCCAGCGTGGTAGGGGCCCCGGTGGCGGTGGTCACTTCCTTGCTGACCGGGCTCTCAACGGCATCCTGCGGGGCGTGC
     3010      3020      3030      3040      3050      3060      3070      3080      3090      3100      3110      3120

Q  P  I  I  E  K  L  A  N  D  Y  A  R  K  I  D  E  L  G  G  P  Q  A  Y  F  E  K  N  L  Q  A  R  H  E  Q  L  A  N  S  D
AGCAGCCCATCATCGAAAAGCTGGCCAACGATTACGCTCGCAAGATCGATGAACTCGGCGGTCCGCAAGCTTACTTCGAGAAAAACCTGCAGGCGCGTCACGAACAACTGGCCAATTCGG
     3130      3140      3150      3160      3170      3180      3190      3200      3210      3220      3230      3240

G  L  R  K  M  L  A  D  L  Q  A  G  H  N  A  S  S  V  I  G  V  Q  T  T  E  I  S  K  S  A  L  E  L  A  A  I  T  G  N  A
ACGGGCCTACGGAAAATGCTGGCCGACCTGCAGGCCGGTCATAACGCCTCCAGTGTGATCGGGGTGCAGACCACAGAGATCTCCAAGTCGGCGCTCGAACTGGCCGCCATTACCGGCAACG
     3250      3260      3270      3280      3290      3300      3310      3320      3330      3340      3350      3360
```

Fig. 3F

```
  D  N  L  K  S  V  D  V  F  V  D  R  F  V  Q  G  E  R  V  A  G  Q  P  V  V  L  D  V  A  A  G  G  I  D  I  A  S  R  K  G
CGGACAACCTGAAATCCGTCGACGTTGTCGTGACCGCTTCGTCCAGGGCGAGCGGGTGGCCGGCCAGCCGGTGGTCCTCGACGTCGCCGCCGGGCATCGATATCGCCAGCCGCAAGG
        3380        3390        3400        3410        3420        3430        3440        3450        3460        3470        3480

E  R  P  A  L  T  F  I  T  P  L  A  A  P  G  E  E  Q  R  R  R  T  K  T  G  K  S  E  F  T  T  F  V  E  I  V  G  K  Q  D
GCGAGCGGCCGGCCCTGACGTTCATCACGCCGCTGGCCGCGCCAGGAGAAGAGCAGCGCCGGCACGAAAACGGGCAAGAGCGAATTCACCACATTCGTCGAGATCGTGGGCAAGCAGG
        3490        3500        3510        3520        3530        3540        3550        3560        3570        3580        3590        3600

R  W  I  R  D  G  A  A  D  T  T  I  D  L  A  K  V  V  S  Q  L  V  D  A  N  G  V  L  K  H  S  I  K  L  D  V  I  G  G
ACCGCTGGCGCATCCGGGACGGCGCCGCCGACACCACGATCGATCTGGCCAAGGTGGTGTCGCAACTGGTCGACGCCAATGGCGTCCTCAAGCACAGCATCAAACTGGATGTGATCGGGCG
        3610        3620        3630        3640        3650        3660        3670        3680        3690        3700        3710        3720

D  G  D  D  V  V  L  A  N  A  S  R  I  H  Y  D  G  G  A  G  T  N  T  V  S  Y  A  A  L  G  R  Q  D  S  I  T  V  S  A  D
GAGATGGCGATGACGTCGTTGCCAATGCTTCGCGCATCCATTATGACGGCGGCGGGCACCAACACGGTCAGTTACGCCGCCCTGGGTCGACAGGATTCCATTACCGTGTCGCCG
        3730        3740        3750        3760        3770        3780        3790        3800        3810        3820        3830        3840

G  E  R  F  N  V  R  K  Q  L  N  N  A  N  V  Y  Y  R  E  G  V  A  T  Q  T  T  A  Y  G  K  R  T  E  N  V  Q  Y  R  H  V  E
ACGGGGAACGTTTCAACGTTGCGCAAGCAGTTGAACAACGCCAACGTGTATTCGGAAGGCGTGGCTACCCAGACAACCGCCTACGGCAAGCGCACCGAGAATGTCCAATACCGCCATGTCG
        3850        3860        3870        3880        3890        3900        3910        3920        3930        3940        3950        3960
```

Fig. 3G

```
  L  A  R  V  G  Q  V  V  E  V  D  T  L  E  H  V  Q  H  I  I  G  G  A  G  N  D  S  I  T  G  N  A  H  D  N  F  L  A  G  G
AGCTGGCCCGTGTCGGGCAAGTGGTGAAGTCGACACGCTCGAGCATGTGCAGCACATCATCGGCGGGGCCGGCAACGATTCGATACCGGCAATGCCCACGACAACTTCCTAGCCGGCG
        3970        3980        3990        4000        4010        4020        4030        4040        4050        4060        4070        4080

S  G  D  D  R  L  D  G  G  A  G  N  D  T  L  V  G  G  E  G  Q  N  T  V  I  G  G  A  G  D  D  V  F  L  Q  D  L  G  V  H
GGTCGGGGGCGACGACAGGCTGGATGGCGGCGCCGGCAACGACACCCTGGTTGGCGGCGAGGGCCAAAACACGGTCATCGGCGGCGACGACGTATTCCTGCAGGACCTGGGGGTAT
        4090        4100        4110        4120        4130        4140        4150        4160        4170        4180        4190        4200

S  N  Q  L  D  G  G  A  G  V  D  T  V  K  Y  N  V  H  Q  P  S  E  E  R  L  E  R  M  G  D  T  G  I  H  A  D  L  Q  K  G
GGAGCAACCAGCTCGATGGCGGCGCCGGCGTCGATACCGTGAAGTACAACGTGCACCAGCCTTCCGAGGAGCGCCTCGAACGCATGGGCGACACGGGCATCCATGCCGATCTTCAAAAGG
        4210        4220        4230        4240        4250        4260        4270        4280        4290        4300        4310        4320

T  V  E  K  W  P  A  L  N  L  F  S  V  D  H  V  K  N  I  E  N  L  H  G  S  R  L  N  D  R  I  A  G  D  D  D  Q  D  N  E  L
GCACGGTCGAGAAGTGGCCGGCCCTGAACCTGTTCAGCGTCGACCATGTCAAGAATATCGAGAATCTGCACGGCTCCCGCCTAAACGACCGCATCGCCGGCGACGACGACCAGGAACGAGC
        4330        4340        4350        4360        4370        4380        4390        4400        4410        4420        4430        4440

W  G  H  D  G  N  D  T  I  R  G  R  G  G  D  D  I  L  R  G  G  L  G  L  D  T  L  Y  G  E  D  G  N  D  I  F  L  Q  D  D
TCTGGGGCCACGATGGCAACGACACGATACGCGGCCGGGGCGGCGACGACATCCTGCGCGGCGGCCTGGGCCTGGACACGCTGTATGGCGAGGACGGCAACGACATCTTCCTGCAGGACG
        4450        4460        4470        4480        4490        4500        4510        4520        4530        4540        4550        4560
```

Fig. 3H

```
E  T  V  S  D  D  I  D  G  G  A  G  L  D  T  V  D  Y  S  A  M  I  H  P  G  R  I  V  A  P  H  E  Y  G  F  G  I  E  A  D
ACGAGACCGTCAGCGATGACATCGACGGCGGCGCTGGACACCGTCGACTACTCCGCCATGATCCATCCAGGCAGGATCGTTGCGCCGCATGAATACGGCTTCGGGATCGAGGCGG
        4570          4580          4590          4600          4610          4620          4630          4640          4650          4660          4670          4680

L  S  R  E  W  V  R  K  A  S  A  L  G  V  D  Y  Y  Y  D  N  V  R  N  V  E  N  V  I  G  T  S  M  K  D  V  L  I  G  D  A  Q
ACCTGTCCAGGGAATGGGTGCGCAAGGCGTCCGCGCTGGGCGTGGACTATTACGATAATGTCCGCAATGTCGAAAACGTCATCGGTACGAGCATGAAGGATGTGCTCATCGGCGACGCGC
        4690          4700          4710          4720          4730          4740          4750          4760          4770          4780          4790          4800

A  N  T  L  M  G  Q  G  G  D  D  T  V  R  G  G  D  G  D  D  L  L  F  G  G  D  G  N  D  M  L  Y  G  D  A  G  N  D  T  L
AAGCCAATACCCTGATGGGCCAGGGCGGCGACGACACCGTGCGCGGCGACGGCGATGATCTGCTGTTCGGCGGCGACGGCAACGACATGCTGTATGGCGACGCCGGCAACGACACCC
        4810          4820          4830          4840          4850          4860          4870          4880          4890          4900          4910          4920

Y  G  G  L  G  D  D  T  L  E  G  G  A  G  N  D  W  F  G  Q  T  Q  A  R  E  H  D  V  L  R  G  G  D  G  V  D  T  V  D  Y
TCTACGGGGGGCTGGGCGACGACACCCTTGAAGGCGGCGCGGGCAACGATTGGTTCGGCCAGACGCAGGCGCGAGACGAGCATGACGTTCTGCGCGGCGGAGATGGGGTGGATACCGTCGATT
        4930          4940          4950          4960          4970          4980          4990          5000          5010          5020          5030          5040

S  Q  T  G  A  H  A  G  I  A  A  G  R  I  G  L  G  I  L  A  D  L  G  A  G  R  V  D  K  L  G  E  A  G  S  S  A  Y  D  T
ACAGCCAGACCGGCGCCATGCCCGGCCATTGCCGCGGTCGACAAGCTGGGCGAGGCCGGCAGCAGCGCCTACGATA
        5050          5060          5070          5080          5090          5100          5110          5120          5130          5140          5150          5160
```

Fig. 31

```
  V  S  G  I  E  N  V  V  G  T  E  L  A  D  R  I  T  G  D  A  Q  A  N  V  L  R  G  A  G  G  A  D  V  L  A  G  G  E  G  D
CGGTTCCGGGTATCGAGAACGTGGTGGGCACGGAACTGGCCGACCGCATCACGGGCGATGCCCAGGCCAACGTGCTGCGCGGGGCCGGTGGCGCCGACGTGCTTGCGGGCGGCGAGGGCG
        5170       5180       5190       5200       5210       5220       5230       5240       5250       5260       5270       5280

D  V  L  L  G  G  D  G  D  D  Q  L  S  G  D  A  G  R  D  R  L  Y  G  E  A  G  D  D  W  F  F  Q  D  A  A  N  A  G  N  L
ACGATGTGCTGCTGGGCGGCGACGGCGACGACCAGCTGTCGGGCGACGCCGGCCGCGACCGCCTGTACGGCGAAGCCGGTGACGACTGGTTCTTCCAGGATGCCGCCAATGCCGGCAATC
        5290       5300       5310       5320       5330       5340       5350       5360       5370       5380       5390       5400

L  D  G  G  D  G  R  D  T  V  D  F  S  G  P  G  R  G  L  D  A  G  A  K  G  V  F  L  S  L  G  K  G  F  A  S  L  M  D  E
TGCTCGACGGCGGCGACGGCCGCGACACCGTGGATTTCAGCGGCCCCGGGCGCGGCCTCGACGCCGGCGCAAAGGGCGTATTCCTGAGCTTGGGCAAGGGTTCGCCAGCTTGATGGACG
        5410       5420       5430       5440       5450       5460       5470       5480       5490       5500       5510       5520

P  E  T  S  N  V  L  R  N  I  E  N  A  V  G  S  A  R  D  D  V  L  I  G  D  A  G  A  N  V  L  N  G  L  A  G  N  D  V  L
AACCCGGAAACCAGCAACGTGTTGCGCAATATCGAGAACGCCGTGGGCAGCGCCCGTGATGACGTGCTGATCGGCGACGCAGGCGCCAACGTCCTCAATGGCCTGGCGGGCAACGACGTGC
        5530       5540       5550       5560       5570       5580       5590       5600       5610       5620       5630       5640

S  G  G  A  G  D  D  V  L  L  G  D  E  G  S  D  L  L  S  G  D  A  G  N  D  D  L  F  G  G  Q  G  D  D  T  Y  L  F  G  V
TGTCCGGCGGCGCTGCAGACGACGTGCTGCTGGGCGACGAGGGCTCCGACCTGCTCAGCGGCGATGCGGGCAACGACGACCTGTTCGGCGGGCAGGGCGATGATACTTATCTGTTCGGGG
        5650       5660       5670       5680       5690       5700       5710       5720       5730       5740       5750       5760

G  Y  G  H  D  T  I  Y  E  S  G  G  H  D  T  I  R  I  N  A  G  A  D  Q  L  W  F  A  R  Q  G  N  D  L  E  I  R  I  L
TCGGGTACGGCCACGACACGATCTACGAATCGGGCGGGCACGACACCATCCGCATCAACGCCGGGGCCGACCAGCTGTGGTTCGCCGCCAGGCAACGACCTGGAGATCCGGATTC
        5770       5780       5790       5800       5810       5820       5830       5840       5850       5860       5870       5880
```

Fig. 3J

```
  G  T  D  D  A  L  T  V  H  D  W  Y  R  D  A  D  H  R  V  E  I  I  H  A  A  N  Q  A  V  D  Q  A  G  I  E  K  L  V  E  A
TCGGCACCGACGATGACTTACCGTGCACACTGGTATCGCGACGCCGATCACGACCATCATCCGCGCCAACCAGGCGGTAGACCAGGCAGGCATCGAAAAGCTGGTCGAGG
     5890      5900      5910      5920      5930      5940      5950      5960      5970      5980      5990      6000

M  A  Q  Y  P  D  P  G  A  A  A  A  P  P  A  A  R  V  P  D  T  L  M  Q  S  L  A  V  N  W  R  *
CAATGGCGCAGTATCCGGACCCCGGCGCGGCAGCGGCTGCCCCCGCCGGCGCCGGACACGCTGCCGGACACGCTGATGCAGTCCCTGGCTGTCAACTGGCGTGAATCACGGCC
     6010      6020      6030      6040      6050      6060      6070      6080      6090      6100      6110      6120

M  T  S  P  A  A  Q  C  A  S  V  P  D  S  G  L  L  C  L  V  M
CGCCTGCCTCGCGCGGCGGGCGCCGTCTCTTTGGCGTTCTTCTCCGAGGTATTCCCATGACGTCGCCCCGGCCAATGCGCCAGCGTGCCCAGCTGCCCGATTCCGGGTTGCTCTGCCTGGTCAT
     6130      6140      6150      6160      6170      6180      6190      6200      6210      6220      6230      6240

L  A  R  Y  H  G  L  A  A  D  P  E  Q  L  R  H  E  F  A  E  R  H  S  V  A  K  R  Y  S  L  A  A  R  R  V  G  L  K  V  R
GCTGGCTCGCTATCACGGATTGGCAGCGGATCCCGAGCAGTTGCGCCATGAGTTCGCCGAGAGGCATTCTGTAGCCAAACGATACAGCCTGGCGGCCCGCCGGGTCGGCCTGAAAGTGCG
     6250      6260      6270      6280      6290      6300      6310      6320      6330      6340      6350      6360

R  H  R  P  A  P  A  R  L  P  R  A  P  L  P  A  I  A  L  D  P  V  G  R  L  I  S
GCGGGCACCGACCGCCCGGCGCGCCTGCCACGCCGGCCATGCCGGCTGACCCCGGTAGGGCGGCTAATTTCTT
     6370      6380      6390      6400      6410      6420      6430      6440

7           17           27           37
```

ADENYL CYCLASE DERIVATIVES AND THEIR BIOLOGICAL USES

BACKGROUND OF THE INVENTION

The subject of the invention is adenyl cyclase derivatives, their preparation by mutagenesis and their biological uses, in particular as vaccines.

Vaccinations against acute infections caused in vertebrates by pathogenic bacteria of the genus Bordetella or *Bacillus anthracis* generally require the utilization of virulent or attenuated whole bacteria.

However, such vaccines are not necessarily devoid of toxicity due to the nature of the diseases caused by these bacteria.

In fact, it is often proteins produced by bacteria, and not the bacteria themselves, which are responsible for the virulence. Even after bacterial death, these proteins may be responsible for many pathological effects.

In the pathology induced by *Bordetella pertussis* a filamentous hemagglutinin (FHA) as well as two toxins lead to an unregulated increase in the production of cyclic AMP in the host cells. These toxins are the pertussis toxin (Ptx or LPF) which activates the cyclase of the host, and the adenyl cyclase, activated by calmodulin (AC).

Finally, a hemolysin is associated with the adenyl cyclase.

The adenyl cyclase of *B. pertussis* was called cyclolysin to point out this fact.

In the light of these observations, the inventors have investigated vaccination agents in which the bacteria of the virulent or attenuated strains are not longer involved, but rather the proteins produced, are modified in an appropriate manner in order to destroy their original toxicity. In particular, adenyl cyclase has been investigated in this respect.

SUMMARY OF THE INVENTION

The aim of the invention is to provide novel derivatives of adenyl cyclase, these derivatives being devoid of toxic activity but being capable of forming antibodies which also recognize the toxic proteins.

It also aims to provide a procedure for preparing these derivatives by in vitro mutagenesis of the genes coding for the toxic adenyl cyclase.

Another aim of the invention consists in the provision of vaccines which ensure an effective protective action against the infections produced by pathogenic agents.

The adenyl cyclase derivatives of the invention are characterized in that they contain one or more amino acids different from those of the toxic protein these changes conferring on them an atoxic character. The amino acids that have been changed are implicated in the catalytic mechanism and/or in the mode of activation by calmodulin and/or the transfer of information from the activator site to the catalytic site of the adenyl cyclase and do not appreciably affect the threedimensional configuration of the toxic protein, so that the antibodies formed against the atoxic derivatives also recognize the toxic protein.

Another characteristic of the invention relates to the whole protein, where the amino acids responsible for the hemolytic activity have been altered or deleted.

BRIEF DESCRIPTION OF THE FIGURES

FIGS. 1a to 1f represent the nucleotide sequence of the active part of the gene coding for the adenyl cyclase of *B. pertussis* and the corresponding amino acid sequence of the adenyl cyclase expressed in *E. coli*.

FIG. 2 represents the complete amino acid sequence of the polypeptide of the adenyl cyclase of *B. anthracis* (upper line) and the N-terminal polypeptide sequence of the adenyl cyclase of *B. pertussis* (lower line).

FIGS. 3a to 3j represent the nucleotide sequence of the active part of the gene coding for the adenyl cyclase of *B. anthracis* and the corresponding amino acid sequence of the adenyl cyclase expressed in *E. coli*.

DESCRIPTION OF THE PREFERRED EMBODIMENTS

The amino acid(s) of replacement are selected in the light of their physico-chemical properties, so as to destroy the toxicity without affecting the structure of the protein appreciably, at least in respect to its recognition by the immune system.

In possessing the same geometry as the toxic protein, these derivatives advantageously play the role of decoy for the immune system without, however, exerting toxic catalytic activity.

Among the properties making it possible to operate on the original toxic character of the protein and to destroy it, mention may especially be made of the size of the amino acids, their hydrophobic or hydrophilic character, their charge, their propensity to form or destroy the secondary structures of the protein their action on the structure of water, their helix-forming or -breaking character, their interaction with all or part of the ATP involved as substrate or with calmodulin.

According to a preferred embodiment of the invention, the adenyl cyclase derivatives contain one or advantageously at least two amino acids replacing wild type amino acids in the catalytic site, i.e. in the domain responsible for the production of cyclic AMP (cAMP). This arrangement makes it possible to suppress the production of cAMP or to make it minimal while conserving the immunogenic properties of the protein.

The different amino acid(s) in the catalytic site are selected more especially to modify the structure of water, or the interaction of the protein with water or with the phosphate, the nucleic base and/or the sugar of the ATP, so that the catalytic activity or the control of this activity of the site is destroyed.

For example, hydrophobic amino acids may be charged with hydrophilic amino acids of the same size or vice versa or amino acids having differing electrical charge may be used, or alternatively amino acids of different size which prevent the introduction of the substrate ATP, or the cyclization reaction to cAMP.

As examples, mention should be made of the replacement of one or at least two lysines, which interact with the ATP, with amino acids of the same volume, hydrophilic but devoid of charge such as glutamine (Q).

Within the catalytic peptide sequence, the GLNVHAKS core may be modified, and G and A each replaced by one of the following amino acids M, L, I, V, or F. As indicated K may be replaced by Q but also by M, L, I, V.

The meanings of the letters commonly used to designate the above amino acids and those mentioned hereafter are given at the end of the description.

The domain responsible for the hemolytic activity may advantageously be deleted in the whole protein, for example by cutting the gene at the Bgl II (AGATCT) sites and by deleting the corresponding fragment. That amounts to removing the portion of the protein situated between EI xxx and EI xxx.

As an additional arrangement, it is possible to take advantage of the fact that the protein does not contain a cysteine residue in order to introduce this amino acid by localized mutagenesis. The latter then may be subject to an appropriate chemical treatment (oxidation for example or reaction with SH reagents of the metallic type, organomercurials or iodoacetamide), the result of which will be the inactivation of the protein.

The different amino acids replacing the wild type amino acids may also be selected from among amino acid analogues which can be incorporated by the translation machine, if necessary, chemically modified. As examples, mention should be made of flourophenylalanine, bromotryptophan, or nor-leucine.

In another embodiment of the invention, which may be implemented, if appropriate, with the above preferred embodiment, the amino acid(s) of replacement are incorporated in the calmodulin activator site, and are selected as a function of the same parameters, in order to make possible a change in the binding to the activating molecule of the host.

Thus, a negatively charged and helix-breaking, hydrophilic aspartic acid residue will advantageously replace a helix-forming and hydrophobic tryptophan residue of larger size in the region of binding to the calmodulin.

In yet another embodiment, implemented alone, or in combination with at least one of those which precede the amino acid(s) of replacement, such as those considered above, are present in the region responsible for the transfer of information from the activator site to the catalytic site.

Preferably, the derivatives of the invention are such as those obtained by expression in a host organism of a gene coding for a protein with adenyl cyclase activity, this gene having been modified in vitro, after cloning, by directed mutagenesis.

In addition to the elements of mutagenesis described below, it is also possible to operate by deletion of known regions of the genome, or by insertion of synthetic oligonucleotides so as to destroy a site endowed with activity.

The derivatives of the invention are more particularly mutants of adenyl cyclase of Bordetella responsible for respiratory diseases of vertebrates such as *B. pertussis* and *B. parapertussis* in man and *B. bronchiseptica* and *B. avium* in animals.

The active part of the toxic adenyl cyclase of *B. pertussis* expressed by the cloned gene has the sequence (I) given in the FIGS. 1a to 1f. This sequence is reported in the application EP 88/401.935.7 of Jul. 25, 1988.

The protein corresponding to the sequence (I), which contains 1706 amino acids, comprises two domains exhibiting two principal activities.

The 400 to 500 amino acids of the N-terminal part are responsible for the adenyl cyclase activity and the 1300 to 1200 of the carboxy-terminal part are responsible for the hemolytic activity and the secstory properties of the protein.

In the catalytically active part responsible for the synthesis of cAMP, the adenyl cyclase appears to be organized in two domains: the N-terminal domain of 25 kDa which contains the catalytic site and the C-terminal domain of 12 kDa more particularly the sequence corresponding to the residues 235-254 which contains the principal binding site to calmodulin.

In another embodiment of the invention, the adenyl cyclase derivatives are mutants of an adenyl cyclase of the type expressed by *B. anthracis*. The nucleotide sequence of the gene coding for this adenyl cyclase and the sequence of this latter are reported in the French application filed today in the names of the applicants, entitled "SEQUENCES OF NUCLEOTIDES EXPRESSING THE ADENYL CYCLASE OF *B. ANTHRACIS*, PROTEINS HAVING THE ACTIVITY OF THIS ADENYL CYCLASE AND BIOLOGICAL USES".

The amino acid sequence of the adenyl cyclase of *B. anthracis* (upper line) shows several regions in common with that secreted by *B. pertussis* (lower line) (see FIG. 2).

The most important similarity corresponds to a peptide of 24 amino acids (from position 342 to position 365 in the adenyl cyclase of *B. anthracis*: GVATKGLNVHGKSSDWGPVAGYIP). This sequence contains five gly residues and the core sequence G—GKS (AKS in *B. pertussis*) which is often found in proteins having an affinity for nucleotides.

Two other regions show a weaker similarity. They correspond in *B. anthracis* to the domains extending from the positions 487 to 501 (PLTADYDLFALAPSL), on the one hand, and from 573 to 594 (DVVNHGTEQDNEEFPEKDNEIF), on the other.

As a variant, the derivatives of the invention are such as those obtained by chemical treatment of the modified sequence of adenyl cyclase.

The invention also relates to polyclonal antibodies directed against these modified adenyl cyclases as well as the monoclonal antibodies capable of recognizing them specifically.

In conformity with the invention, the adenyl cyclase derivatives defined above are obtained by in vitro mutagenesis of the cloned gene expressing the toxic protein, followed by expression of the gene in appropriate hosts, for example *E. coli*, *B. avium*, or *Alcaligenes eutrophus* with a subsequent chemical treatment if necessary (particular case of the proteins with cysteine, for example). This expression is carried out in high yields in particular in *E. coli*. The gene can be reintroduced into the pathogenic bacterium in order for it to express the atoxic protein. The bacterium thus modified also is part of the invention.

The procedure for the preparation of the atoxic adenyl cyclase derivatives according to the invention comprises the in vitro mutagenesis of the cloned gene expressing the toxic adenyl cyclase. This mutagenesis is carried out in the region coding for the catalytic site, and/or the calmodulin activator site and/or the site responsible transfer of information from the calmodulin activator site to the catalytic site and/or the region responsible for the hemolytic activity. The mutagenesis introduces one or more codons coding for amino acids different from these present in the toxic protein, or deletes codons present in the original gene to confer on the mutant an atoxic character without appreciably affecting its three dimensional configuration shown by the toxic protein, to permit antibodies formed against the atoxic derivatives to also recognize the toxic protein.

The mutagenesis advantageously affects the codons coding for the amino acids defined above.

According to a preferred embodiment of the invention, the system of in vitro mutagenesis implemented is that of Amersham or any other company offering systems of the same type comprising the utilization of a mutant oligonucleotide to direct the mutagenesis. This oligonucleotide is constructed to include the codon encoding the amino acid which is desired to be introduced. The desired final codon may be introduced in a single step, or through an introduction of an intermediary codon, then in a later step, to the introduction of the desired final codon.

As an alternative, it is also possible to use a mutant oligonucleotide containing an ambiguity and thus capable of coding for two different amino acids. Similarly, it is possible to use an oligonucleotide which lacks one or more codons, to produce a deletion.

The mutant oligonucleotide advantageously contains at least fifteen, and in particular from twenty to twenty-five, nucleotides. In conformity with the standard method of in vitro mutagenesis, utilizing the Amersham kit, the following steps are performed:

hybridization of the mutant oligonucleotide to a DNA sequence of a single-stranded DNA matrix appropriately constructed from a vector by in vitro mutagenesis. A phage, in particular a derivative of M 13, is advantageously utilized as DNA single-stranded vector;

synthesis in the presence of a thio-dCTP and ligation to the mutant DNA strand with a polymerase such as the Klenow fragment of the DNA polymerase I of *E. coli*.

removal of the non-mutant single-stranded DNA, for example by filtration;

cleavage of the non-mutant DNA strand with the aid of a restriction enzyme, such as Ncil;

digestion of the non-mutant strand with the aid of an exonuclease, in particular exonuclease III;

repolymerization and ligation of the partially defective DNA;

transformation of competent cell hosts with the DNA.

This procedure has the advantage of giving rise to the atoxic derivative in high yield. It is clear, however, that other embodiments of the mutagenesis for example utilizing restriction sites in order to create insertions, deletions, or replacements, can be implemented so that modifications can be made to the method based on the utilization of the kit sold by Amersham in order to introduce suitable codons and to obtain the atoxic adenyl cyclase derivatives of the invention.

The gene coding for the adenyl cyclase expressed by one of the microorganisms mentioned above is advantageously cloned according to the procedure described in the application Fr 87/10614 of Jul. 24, 1987 in the name of the applicants.

In this procedure, use is made of the adenyl cyclase-calmodulin interaction which is expressed by the production of cAMP. The cloning of the gene is carried out in a receptor strain deficient in adenyl cyclase, carrying a plasmid expressing high levels of calmodulin. It should be noted that the genes which cooperate in this cloning procedure, namely the one which codes for the adenyl cyclase and the one which codes for calmodulin, are of different origins.

The cloned DNA fragment of the active part of the gene coding for the adenyl cyclase of *B. pertussis*, which can be used in the mutagenesis procedure of the invention, corresponds to the sequence of the active part of the genes coding for the adenyl cyclase of *B. Pertussis* and *B. anthracis* respectively as shown in the FIG. 1*a* to 1*f* or also 3*a* to 3*j*.

The catalytic part for the synthesis of cAMP of the DNA fragment includes the sequence of nucleotides localized between the positions 0 and 2050, with the position 0 corresponding to the BamHI restriction site.

Any sequence of nucleotides which hybridizes with the sequence of nucleotides of FIGS. 1*a* to 1*f* or 3*a* to 3*j* and codes for a protein with adenyl cyclase activity, whether this sequence is obtained by reverse enzymatic transcription of the corresponding RNA or by chemical synthesis, can be used in the procedure according to the invention for the purposes of mutagenesis.

The invention also relates to nucleotides sequences comprising or constituted by the gene coding for at least the active part of an adenyl cyclase, but mutated so as to code for an adenyl cyclase derivative such as that defined above as well as the mutant oligonucleotides.

Thus, in relation to the DNA fragment of the FIGS. 1*a* to 1*f*, a nucleotide sequence according to the invention contains a CAA codon in the place of the AAA codon at position 58, or also a CAG codon in the place of the AAG codon at position 65. Preferably, these oligonucleotides are unable to make possible a nonspecific hybridization with the vector M13.

The mutant oligonucleotides contain for example a CAA codon in the place of a AAA codon at position 58 and contain all or part of the sequence GTG GCC ACC CAA GGA TTG G.

It may also involve oligonucleotides with a CAG codon in the place of a AAG codon at position 65 and containing all or part of the sequence GTGCACGCCCAGTCGTCCG.

Other oligonucleotides contain instead of a TGG condon at position 242 a GAC codon and correspond to all or part of the sequence CTTGTTGGACAAAATCGC, or a GAC codon in the place of the GAC codon of the preceding oligonucleotide.

A mixture of oligonucleotides can make it possible to obtain several mutants in a single experiment.

As an alternative, the atoxic derivatives of the invention may be obtained by subjecting the protein sequence of an adenyl cyclase, or at least its active part, to a chemical treatment. For example, the inactivation treatments used in vaccination, such as in the case of tetanus vaccinations.

The toxicological assays carried out on the protein derivatives of the invention have demonstrated the absence of toxicity.

The strongly immunogenic properties of the derivatives of the invention are thus advantageously taken advantage of for the development of vaccines.

The vaccines of the invention are characterized in that they are molecular vaccines containing at least one atoxic derivative of adenyl cyclase such as that defined above, in combination with a pharmaceutical vehicle.

They may also contain the bacterium carrying the mutated genes and thus rendered atoxic.

Vaccination is carried out according to the usual dosages and with the usual forms of administration.

In an advantageous manner, the adenyl cyclase derivatives of the invention give rise to an immunological cross-reaction with antibodies directed against the adenyl cyclase of *B. pertussis*. Advantageous compositions of vaccines contain the adenyl cyclase derivative of the invention in combination with a preparation of killed *B. pertussis* bacteria used as adjuvant.

In order to illustrate the invention, examples are reported below of the preparation of adenyl cyclase mutants of *B. pertussis*. In these examples, reference is made to the FIG. 1a to 1f and 3a to 3j, which present the nucleotide sequences of the active part of the gene coding for the adenyl cyclase of *B. pertussis* and *B. anthracis*, respectively, cloned in *E. coli* and the corresponding amino acid sequence expressed, and to FIG. 2 which shows the complete sequence of the polypeptide of the adenyl cyclase of *B. anthracis* (upper line) and the N-terminal polypeptide sequence of the adenyl cyclase of *B. pertussis* (lower line).

EXAMPLE

1. Cloning of the gene coding for the adenyl cyclase of *B. pertussis*.

cya⁻, restriction⁻ strains of *E. coli* are transformed by a plasmid carrier of a gene specifying the synthesis of calmodulin such as the plasmid pVUC-1, or any other plasmid expressing the calmodulin of the incompatibility group ColE1 and carrier of the gene for resistance to ampicillin.

Into the cya⁻ strains are then introduced vectors containing the DNA of *B. pertussis* completely fragmented in various ways (partial cleavages by the restriction enzymes EcoRI and SauIIIa, sonication followed by addition of EcoRI "linkers", for example).

In view of the problems posed by the incompatibility of other plasmids having the ColEI replicon, the cloning of fragments of the total DNA of *B. pertussis* partially cleaved by the enzyme SauIIIa was carried out in the compatible vector pACYC184, at the unique BamH1 site. The receptor strains were transformed and spread on McConkey Maltose plates. Several clones fermenting maltose were isolated. It was then demonstrated that these clones produce cyclic AMP. Moreover, the plasmids extracted from the producer strains were integrated by transformation into strains which do not contain the plasmid pVUC-1 or do contain it. In the former case, the clones are white on the McConkey maltose media, red in the latter, confirming that it is indeed the presence of the plasmids giving rise to the synthesis of calmodulin which has made the cloning possible.

2. In vitro mutagenesis of the cloned gene coding for the adenyl cyclase.

By operating as described by Carter et al. in Nucl. Acids Res. 13, 4431–43, 1985, a AAA codon (coding for K) is replaced by a CAA codon (coding for Q) at position 58 by using the oligonucleotide GTGGCCACC-CAAGGATTGG. Similarly, a AAG codon (coding for K) at position 65 is replaced by a CAG codon (coding for Q) by utilizing the oligonucleotide GTGCACGCCCAGTCGTCCG.

The two modifications are carried out on the DNA fragment BamHI-EcoRV cloned in the phage M13tg130.

The TGG codon at position 242 (coding for tryptophan) is first modified to a GAC codon (coding for aspartic acid) by using the oligonucleotide CTTGTTGGACAAAATCGC. The GAC codon is then modified to a GAG codon (coding for glutamic acid) by using the oligonucleotide CTTGTTGGAGAAAATCGC. It should be noted that in this case the mutagenesis affects a codon which is not found in a zone of similarity with the nucleotide sequences of other genes coding for an adenyl cyclase, more particularly that of *B. anthracis*.

The modifications at position 242 were carried out on the DNA fragment EcoRV-EcoRI cloned in the phage M13tg130.

For each mutagenesis, a control is performed on the mutated fragment for the absence of any other mutation by the method of sequencing with a dideoxynucleotide.

3. Preparation of the atoxic derivatives of adenyl cyclase.

By expression of the mutated gene in an *E. coli* strain according to conventional techniques the atoxic adenyl cyclase is obtained which is then purified.

It will be noted that the replacement of tryptophan by aspartate reduces by a factor of 1,000 the activatability of the enzyme by calmodulin, while its basal activity is maintained.

The replacement of lysine at position 65 diminishes the intrinsic basal activity of the enzyme by a factor of at least 100.

The single letters used to designate the amino acids have the following meanings:

| | |
|---|---|
| Aspartic acid | D |
| Glutamic acid | E |
| Alanine | A |
| Arginine | R |
| Asparagine | N |
| Cysteine | C |
| Glutamine | Q |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

We claim:
1. An adenyl cyclase derivative wherein:
(a) the amino acid sequence of said derivative consists essentially of an amino acid sequence of a *Bacillus anthracis* adenyl cyclase comprising an amino acid substitution in at least one site of said derivative, wherein said sites are selected from the group consisting of amino acids 342–365 of the *Bacillus anthracis* sequence of FIG. 2 and the calmodulin binding site, and said amino acid substitution is selected from the group consisting of:
i) a replacement of a lysine residue with an amino acid selected from the group consisting of glutamine, asparagine, aspartic acid, glutamic acid, methionine, leucine, isoleucine, and valine;
ii) a replacement of a tryptophan residue with an amino acid selected from the group consisting of aspartic acid, glutamic acid, asparagine, and glutamine; and
iii) a replacement of a lysine residue as indicated in i) and a replacement of a tryptophan residue as indicated in ii); and
(b) said derivative is atoxic.
2. An adenyl cyclase derivative, wherein:
(a) the amino acid sequence of said derivative consists essentially of an amino acid sequence of a *Bordetella pertussis* adenyl cyclase comprising an amino acid substitution in at least one site of said deriva- tive, wherein said sites are selected from the group consisting of amino acids 54-77 of the *Bordetella pertussis* sequence of FIG. 2 and the calmodulin binding site, and said amino acid substitution is selected from the group consisting of:
  i) a replacement of a lysine residue with an amino acid selected from the group consisting of glutamine, asparagine, aspartic acid, glutamic acid, methionine, leucine, isoleucine, and valine;
  ii) a replacement of a tryptophan residue with an amino acid selected from the group consisting of aspartic acid, glutamic acid, asparagine, and glutamine; and
  iii) a replacement of a lysine residue as indicated in i) and a replacement of a tryptophan residue as indicated in ii).

3. The adenyl cyclase derivative of claim 1 or 2, wherein said amino acid substitution comprises a replacement of a lysine residue of said adenyl cyclase with an amino acid selected from the group consisting of glutamine, asparagine, aspartate, and glutamate.

4. The adenyl cyclase derivative of claim 1 or 2, wherein the amino acid sequence of said derivative further comprises an amino acid analogue selected from the group consisting of fluorophenylalanine, bromotryptophan, and norleucine in said sites.

5. The adenyl cyclase derivative of claim 2, wherein said amino acid substitution comprises a replacement of a tryptophan residue with an amino acid selected from the group consisting of aspartate, glutamate, asparagine, and glutamine, wherein said replacement is in the calmodulin binding domain.

6. An adenyl cyclase derivative of *Bordetella pertussis* wherein the amino acid sequence of said derivative consists essentially of an amino acid sequence of *Bordetella pertussis* adenyl cyclase comprising a replacement of lysine at position 58 according to the *Bordetella pertussis* sequence of FIG. 2 with glutamine.

7. An adenyl cyclase derivative of *Bordetella pertussis*, wherein the amino acid sequence of said derivative consists essentially of an amino acid sequence of *Bordetella pertussis* adenyl cyclase comprising a replacement of lysine at position 65 of the *Bordetella pertussis* sequence of FIG. 2 with glutamine.

8. An adenyl cyclase derivative of *Bordetella pertussis*, wherein the amino acid sequence of said derivative consists essentially of an amino acid sequence of *Bordetella pertussis* adenyl cyclase comprising a replacement of tryptophan at position 242 of the *Bordetella pertussis* sequence of FIG. 2 with an amino acid selected from the group consisting of aspartic acid and glutamic acid.

9. An adenyl cyclase derivative of *Bacillus anthracis*, wherein the amino acid sequence of said derivative consists essentially of an amino acid sequence of *Bacillus anthracis* adenyl cyclase comprising a replacement of lysine at position 346 of the *Bacillus anthracis* sequence of FIG. 2 with glutamine.

10. An adenyl cyclase derivative of *Bacillus anthracis*, wherein the amino acid sequence of said derivative consists essentially of an amino acid sequence of *Bacillus anthracis* adenyl cyclase comprising a replacement of lysine at position 353 of the *Bacillus anthracis* sequence of FIG. 2 with glutamine.

11. An adenyl cyclase derivative of *Bordetella pertussis*, wherein the amino acid sequence of said derivative comprises a substitution of the amino acid sequence GLNVHAKS of the catalytic site of *Bordetella pertussis* with the amino acid sequence:

$R_1$ LNVHR$_1$R$_2$S wherein
  $R_1$ is selected from the group consisting of M, L, I, V, and F; and
  $R_2$ is selected from the group consisting of Q, N, D, E, M, L, I, and V.

12. A nucleotide sequence encoding the adenyl cyclase derivative of claim 1.

13. A process for obtaining an atoxic adenyl cyclase derivative, wherein said process comprises:
  (a) providing a host cell transformed with a vector comprising a DNA sequence of a mutant gene of an adenyl cyclase, wherein:
    i) said DNA sequence encodes an atoxic adenyl cyclase;
    ii) said DNA sequence encodes an amino acid sequence of a *Bacillus anthracis* adenyl cyclase comprising an amino acid substitution in at least one site of said derivative, wherein said sites are selected from the group consisting of amino acids 342-365 of the *Bacillus anthracis* sequence of FIG. 2 and the calmodulin binding site, and said amino acid substitution is selected from the group consisting of:
      1) a replacement of a lysine residue with an amino acid selected from the group consisting of glutamine, asparagine, aspartic acid, glutamic acid, methionine, leucine, isoleucine, and valine;
      2) a replacement of a tryptophan residue with an amino acid selected from the group consisting of aspartic acid, glutamic acid, asparagine, and glutamine; and
      3) a replacement of a lysine residue as indicated in 1) and a replacement of a tryptophan residue as indicated in 2); and
  b) expressing said atoxic adenyl cyclase derivative in the host cell.

14. The process of claim 13, wherein said host cell is *Escherichia coli*.

15. A process for obtaining an atoxic adenyl cyclase derivative, wherein said process comprises:
  (a) providing a host cell transformed with a vector comprising a DNA sequence of a mutant gene of an adenyl cyclase, wherein:
    i) said DNA sequence encodes an atoxic adenyl cyclase;
    ii) said DNA sequence encodes an amino acid sequence of a *Bordetella pertussis* adenyl cyclase, comprising an amino acid substitution in at least one site of said derivative wherein said sites are selected from the group consisting of amino acids 54-77 of the *Bordetella pertussis* sequence of FIG. 2 and the calmodulin binding site, and said amino acids substitution is selected from the group consisting of:
      1) a replacement of a lysine residue with an amino acid selected from the group consisting of glutamine, asparagine, aspartic acid, glutamic acid, methionine, leucine, isoleucine, and valine;
      2) a replacement of a tryptophan residue with an amino acid selected from the group consisting of aspartic acid, glutamic acid, asparagine, and glutamine; and 3) a replacement of a lysine residue as indicated in 1) and a replacement of a tryptophan residue as indicated in 2); and (b) expressing said atoxic adenyl cyclase derivative in the host cell.

16. The process of claim 15, wherein said amino acid substitution comprises a replacement of lysine at position 58 of the *Bordetella pertussis* sequence of FIG. 2 with glutamine.

17. The process of claim 15, wherein said amino acid substitution comprises a replacement of lysine at position 65 of the *Bordetella pertussis* sequence of FIG. 2 with glutamine.

18. The process of claim 15, wherein said amino acid substitution comprises a replacement of tryptophan at position 242 of the *Bordetella pertussis* sequence of FIG. 2 with an amino acid selected from the group consisting of aspartic acid and glutamic acid.

* * * * *